(12) United States Patent
Werlink

(10) Patent No.: US 10,562,071 B2
(45) Date of Patent: Feb. 18, 2020

(54) SYSTEM FOR STRUCTURAL HEALTH MONITORING AND/OR NON-INVASIVE TANK FLUID LEVEL MEASUREMENT INCLUDING CRYOGENIC AND ZERO G ENVIRONMENTS

(71) Applicant: Rudolph J. Werlink, Winter Springs, FL (US)

(72) Inventor: Rudolph J. Werlink, Winter Springs, FL (US)

(*) Notice: Subject to any disclaimer, the term of this patent is extended or adjusted under 35 U.S.C. 154(b) by 132 days.

(21) Appl. No.: 15/648,761

(22) Filed: Jul. 13, 2017

(65) Prior Publication Data

US 2018/0001350 A1 Jan. 4, 2018

Related U.S. Application Data

(63) Continuation-in-part of application No. 15/450,472, filed on Mar. 6, 2017, now abandoned.
(Continued)

(51) Int. Cl.

| | |
|---|---|
| *B06B 1/16* | (2006.01) |
| *H01L 41/09* | (2006.01) |
| *B06B 1/20* | (2006.01) |
| *B06B 1/06* | (2006.01) |
| *G01N 29/46* | (2006.01) |
| *G01N 29/04* | (2006.01) |
| *G01N 29/34* | (2006.01) |

(Continued)

(52) U.S. Cl.
CPC ............ *B06B 1/165* (2013.01); *B06B 1/0614* (2013.01); *B06B 1/20* (2013.01); *G01H 3/04* (2013.01); *G01N 29/00* (2013.01); *G01N 29/043* (2013.01); *G01N 29/2437* (2013.01); *G01N 29/348* (2013.01); *G01N 29/46* (2013.01); *H01L 41/09* (2013.01); *H01L 41/0926* (2013.01); *G01N 2291/0258* (2013.01); *G01N 2291/02827* (2013.01); *G01N 2291/048* (2013.01); *G01N 2291/103* (2013.01)

(58) Field of Classification Search
CPC ......... B06B 1/165; B06B 1/0614; B06B 1/20; G01H 3/04; G01N 29/00
USPC ........................................................... 73/579
See application file for complete search history.

(56) References Cited

U.S. PATENT DOCUMENTS 4,350,916 A * 9/1982 August ................... H03H 3/08
310/313 B
6,629,341 B2 10/2003 Wilkie et al.
(Continued)

*Primary Examiner* — Tarun Sinha
(74) *Attorney, Agent, or Firm* — Peter J. Van Bergen

(57) ABSTRACT

A system includes a first transducer configured as an actuator. The first transducer is in communication with a surface of a structure. A second transducer is configured as a sensor. The second transducer is in communication with the surface. A third transducer is configured as a sensor. The third transducer is in communication with the surface and separated from the second transduce by an area. A digitizing unit receives signals from the second transducer and the third transducer. The digitizing unit communicates a plurality of frequency signals for the first transducer. A computing unit communicates the plurality of frequency signals to the digitizing unit, receives digitized signals from the digitizing unit, and calculates a Frequency Response Function from the digitized signals. Changes to the Frequency Response Function indicate a change to physical properties of the structure.

13 Claims, 7 Drawing Sheets

Related U.S. Application Data

(60) Provisional application No. 62/304,825, filed on Mar. 7, 2016.

(51) Int. Cl.
*G01N 29/24* (2006.01)
*G01H 3/04* (2006.01)
*G01N 29/00* (2006.01)

(56) References Cited

U.S. PATENT DOCUMENTS

| | | | | |
|---|---|---|---|---|
| 2008/0236275 A1* | 10/2008 | Breed | B60C 11/24 | |
| | | | | 73/290 V |
| 2008/0319688 A1* | 12/2008 | Kim | H04Q 9/00 | |
| | | | | 702/51 |
| 2010/0324839 A1* | 12/2010 | Martin | G01M 3/243 | |
| | | | | 702/56 |
| 2012/0269031 A1* | 10/2012 | Huffman | G01N 29/245 | |
| | | | | 367/7 |

* cited by examiner

SYSTEM FOR STRUCTURAL HEALTH MONITORING AND/OR NON-INVASIVE TANK FLUID LEVEL MEASUREMENT INCLUDING CRYOGENIC AND ZERO G ENVIRONMENTS

CROSS-REFERENCE TO RELATED APPLICATIONS

The present continuation patent application claims priority benefit of the U.S. provisional application for patent Ser. No. 15/450,472 entitled CTIVEVIBRATION SIGNATURE STRUCTURAL FAULT MONITORING AND ZERO G TANK FLUID QUANTITY MEASUREMENT SYSTEM FOR AMBIENT AND CRYOGENIC ENVIRONMENTS", filed 6 Mar. 2017 under 35 U.S.C. 120 and U.S. provisional application for patent Ser. No. 62/304,825 entitled "ACTIVE VIBRATION SIGNATURE STRUCTURAL FAULT MONITORING AND ZERO G TANK FLUID QUANTITY MEASUREMENT SYSTEM FOR AMBIENT AND CRYOGENIC ENVIRONMENTS" filed on 7 Mar. 2016 under 35 U.S.C. 119(e). The contents of these related applications are incorporated herein by reference for all purposes to the extent that such subject matter is not inconsistent herewith or limiting hereof.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to the use of vibration signatures to monitor an instrumented structure or tank. More particularly, certain embodiments of the invention relates to structural health monitoring and/or non-invasive tank fluid level measurement including cryogenic and zero g environments.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is believed that verification of structural integrity by current methods may be either too expensive, too time consuming (requiring highly trained analysts (ultrasonic, thermographs, x-ray, piezo sensor impedance) and/or may show all types of faults including non-critical areas which may require interruption and become highly complex to allow a system which provides a near real time in-Sutu software based indicator when the structure has dangerous defects and may fail. It is believed that current methods of health monitoring and non-destructive evaluation may actively rely on electromagnetic waves or sound waves from an active source in the structure and analyze the reflections or interference caused by defects or passive methods that use the energy released as defects occur to listen to the released energy.

It is believed that current methods to determine the amount of fluid in a tank may require penetrations for the sensors which may allow leakage and in cryogenic fluids to contribute to heat loss. It is believed that in micro-gravity (very low g) environments such as space flight the fluid often moves about (floats) in the container and may prevent existing methods from accurate measurement.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. This invention uses a piezoelectric transducer to vibrate a membrane which is affected in its response by damping of a liquid.

By way of educational background, another aspect of the prior art generally useful to be aware of is that a method includes providing time series structural response data from a structure.

By way of educational background, another aspect of the prior art generally useful to be aware of is that an active damage interrogation (ADI) system (and method) utilizes an array of Piezoelectric transducers attached to or embedded within the structure for both actuation and sensing.

By way of educational background, another aspect of the prior art generally useful to be aware of is that a system and method for structural health monitoring (SHM) of a physical structure, such as an aircraft component, is described. The system may comprise a central data acquisition module and a plurality of wireless, self-contained sensor wafers bonded to a surface of the physical structure.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
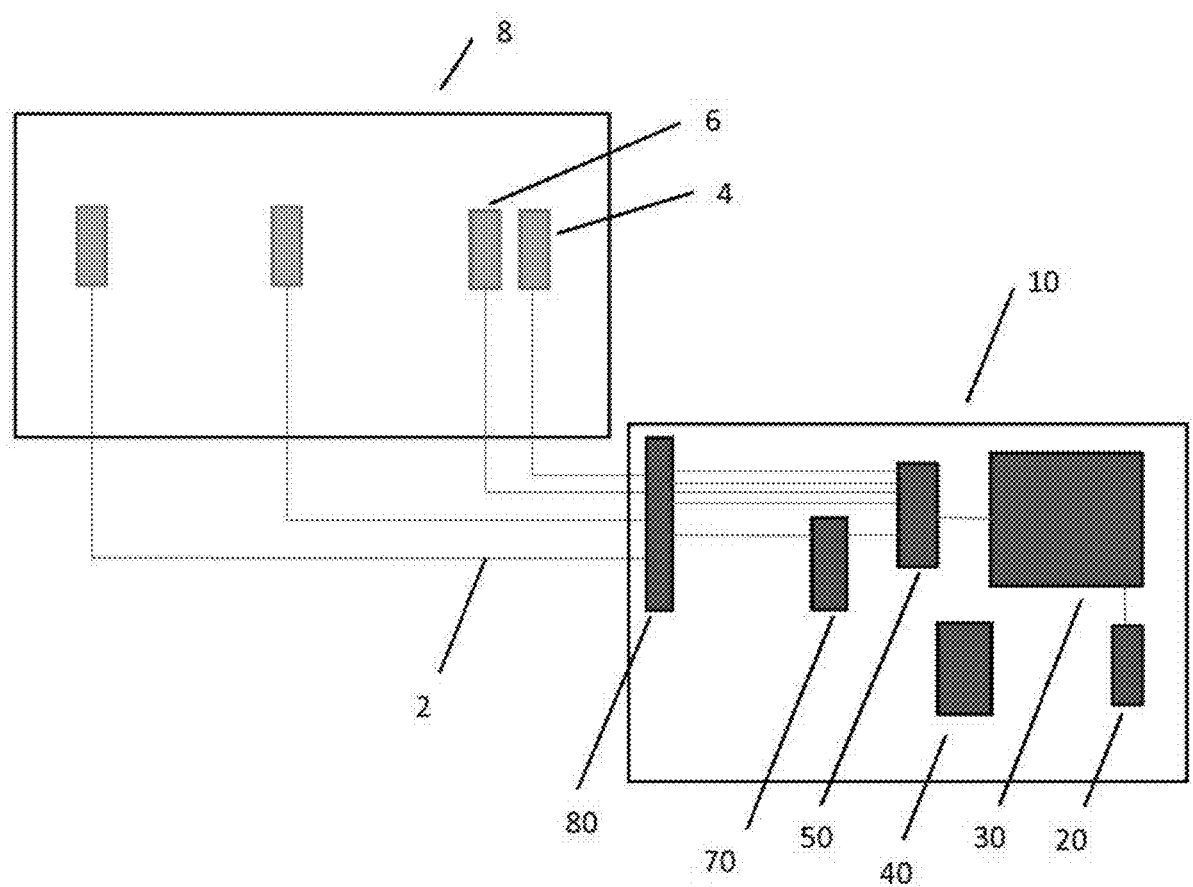
FIG. 1 is an illustration of an exemplary overall system layout of the invention includes optional switch box, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of Claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter.", e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks "Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini.™., C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Additionally, the phrase "configured to" or "operable for" can include generic structure (e.g., generic circuitry) that is manipulated by software and/or firmware (e.g., an FPGA or a general-purpose processor executing software) to operate in a manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

Many embodiments of the present invention, and variations thereof, uses a board band combination of frequencies such as, but not limited to, random white noise, to excite structure natural frequencies and record a signature. In many embodiments, by comparing the signature of an initial condition a change related to stiffness or mass may be observed. This variation may be used to show when a structure has been damaged (less stiffness) or has changed in mass. In many embodiments, transducers used as an actuator and sensors are piezoelectric which generate an electric charge when strained and conversely change length when a charge is applied. If the applied voltage is alternating the transducer vibrates the surface it is mounted on. If the surface has varying strain movement the Piezo acts as a sensor generating a voltage.

In many embodiments, a system of sensors and an actuator may be applied. The recorded data may be processed to transform data from the time domain to the frequency domain. In a non-limiting example, frequency analysis may transform a block of time series samples into a amplitude vs frequency array using the mathematical function fast Fourier transform (FFT), the response sensor FFT data may be divided by the FFT of a sensor near the actuator providing a frequency response function (FRF) between the two points and representing the vibrational frequencies of the underlying structure. Any two sensors may also be compared providing a signature representing the stiffness and mass in that area. The FRF signatures may be compared from previous or baseline responses at various times corresponding to periods of time or after events which could degrade the structure. The structural may include fluid and gas filled tanks, pipes made out of any material, but especially of interest are composites. The frequencies of interest may be over ranges up to the region considered ultrasonic such as, but not limited to, (1-50,000) HZ. The range may depend on the structure. The theory which is believed to be well established is summarized below:

The force generated by the mass is proportional to the acceleration of the mass as given by Newton's second law of motion:

$$\Sigma F = ma = m\ddot{x} = m\frac{d^2x}{dt^2}.$$

The sum of the forces on the mass then generates this ordinary differential equation: $m\ddot{x}+kx=0$, Simple harmonic motion of the mass-spring system assuming that the initiation of vibration begins by stretching the spring by the distance of A and releasing, the solution to the above equation that describes the motion of mass is:

$x(t)=A \cos(2\pi f_n t)$.

This solution says that it will oscillate with simple harmonic motion that has an amplitude of a frequency of FN. The number fn is called the un-damped natural frequency. For the simple mass-spring system, fn is defined as:

$$f_n = \frac{1}{2\pi}\sqrt{\frac{k}{m}}.$$

Note: angular frequency $\omega$ ($\omega=2\pi f$) with the units of radians per second is often used in equations because it simplifies the equations, but is normally converted to ordinary frequency (units of Hz or equivalently cycles per second) when stating the frequency of a system. If the mass and stiffness of the system is known, the formula above may determine the frequency at which the system vibrates once set in motion by an initial disturbance. It is believed that every vibrating system has one or more natural frequencies that it vibrates at once disturbed. This simple relation may be used to understand in general what happens to a more complex system once mass or stiffness may be added.

The signatures which this method produces may be complex and have multiple frequencies which may overlay and may be based of the Fn equation above. The Frequency Response Function (FRF) may minimize noise and may have high sensitivity to the underlying stiffness and modal mass of the structure. It is believed that traditional modal testing and analysis may be usually interested in the lower range of modes or frequencies encompassing the whole-body modes. Many embodiments of the present invention consider a wider range of higher frequencies which may be useful for detecting stiffness changes using local modes. In many embodiments, the sensors are in-Sutu, function as an actuator or sensor depending on whether a voltage is applied or read. In many embodiments, with associated amplifier, data acquisition, computer and unique software and communication (wired or wireless), the present invention may be integrated onto the structure or tank. In many embodiments, the data may be remotely monitored. In many embodiments, the analysis routines, which use FRF comparisons to previous signatures, mode frequency shifts may be identified. Many embodiments may use FFT and FRF averages to reduce noise such as, but not limited to, vibration or fluid movement in the tank. In some embodiments, time domain processing such as, but not limited to, differentiation, integration, averaging, etc. May be applied prior to FFT to reduce noise. In some embodiments, cross correlation may also be used between the FRF signatures. In some embodiments, the programmed mathematical functions including FFT and FRF mode areas, magnitudes and statistical functions including standard deviation, variance may provide a good vs damaged software alert. In the tank fluid volume embodiments may provide a remote indication of fluid volume even in weightless environments. In some embodiments, the two applications may be combined as in, but not limited to, a space flight composite tank which may hold cryogenic fluids, providing very valuable embodiments allowing practical health monitoring of advanced materials and fluid volume determination.

Many embodiments of the present invention, includes the In-Sutu non-invasive and operation over cryogenic temperatures with software automatous go/no go aspect. Some unique design aspects of the present invention include the mathematical methods and frequency ranges used to determine variations from the reference baseline signatures along with the type and installation of the sensors along with the electronics, such as, but not limited to, amplifier, data acquisition, selection circuitry, power collection and storage.

Many embodiments of the present invention may comprise an active random vibration actuator which may provide a wide range of frequencies with the structural stiffness and mass affecting the responses or modes of frequencies which may be recorded by response sensors. The data may be analyzed in the frequency domain using FFT and FRF methods looking for changes in responses from prior vibration signatures or fingerprints. In many embodiments, the actuator and sensors may be the same construction utilizing the piezoelectric effect in a thin flexible construct in piezoelectric ceramic formulations such as, but no limited to, lead zirconate titanate (PZT). Many embodiments may incorporate design features such as, but not limited to, Interdigitated Electrodes. Many embodiments of this invention may be highly useful on composite structures and tanks as these advanced materials may fail suddenly unlike metals with yield in predictable ways.

Embodiments of the present invention have been demonstrated on wind blades tested under fatigue loading, composite and Composite Overwrap Pressure Vessels (COPV) tanks tested to failure using water and cryogenic fluids (liquid nitrogen) substituting for spaceflight propulsion liquid hydrogen/liquid oxygen. The applications of composite tanks/structures may include transportation applications developed to produce very low carbon or zero carbon emissions such as, but not limited to, fuel cells Some embodiments may be applicable for testing integrity of storage batteries such as, but not limited to, Lithium ion packs, etc.

In some embodiments, to measure tank fluid mass the actuator and sensors may be attached to the outer tank wall (non-intrusive) and using a baseline signature compared to known fluid volumes a frequency shift may be measured which represents a known fluid mass. After this calibration, the frequency mode shifts may provide an indicator of amount of fluid. The present invention works in micro-g environments due to the surface tension effects on the floating fluid which causes fluid contact to the inner tank wall affecting the signature in a predicable way. The shift in frequency is directly related to the amount of fluid in contact with the wall and it's mass. Accuracy has been demonstrated to be within several percent over a wide fill range in parabolic plane flight experiments.

FIG. 1 is an illustration of an exemplary overall system layout of the invention includes optional switch box, in accordance with an embodiment of the present invention. The overall system layout of the present invention may include optional digitally controlled relay unit 80. Shown is the structure, pipe or tank to be monitored, 8 with piezoelectric transducers attached to the surface, sensors 6 or actuators 4 depending on whether a varying voltage is applied and the transducer vibrates (actuator) or the transducer is strained (sensor) with a self-generating voltage produced. In some embodiments, the piezoelectric transducers 4 or 6 may be of various designs with the common characteristic of utilizing the piezoelectric effect, with their function as either actuator or sensors interchangeably. In some embodiments, a flexible patch configuration is utilized with the active element consisting of Lead Zirconium Titinate (PZT) (PbTiO3 chemical formula). In some embodiments, the transducers may be attached temporary using such as, but not limited to, double backed tape or permanently using such as, but not limited to, adhesives. In some embodiments, on various materials and geometries made of composites such as, but not limited to, carbon fiber based, under widely varying temperatures including cryogenic ranges (about 100-5 degrees kelvin) cryogenic epoxies may be used. In other applications, up to about 250 degrees F. may be used with suitable adhesives.

In many embodiments, the spacing and number of the transducers used may be dependent on the structure, tank size, materials and geometry. In some embodiments, the spacing and number of transducers may be largely determined experimentally often limited by the amount of noise and effects on the modal peaks of interest. In other embodiments, mathematical models such as, but not limited to, finite elements may be used to predict the best locations and numbers to some accuracy. In many embodiments, the actuator will be able to produce strong enough vibrations over the required frequencies to stimulate important modes or FRF responses which envelope the flaw or defect caused frequencies and stiffness changes. In some embodiments, required frequencies may be largely determined experimentally, often by varying the mass or stiffness known amount and compared to a baseline In other embodiments, mathematical models such as finite elements may be used to predict the frequencies to some accuracy. In the present invention, electronics are shown in a block diagram 10. Wires 2 may connect each transducer to the optional relay unit 80 to the digitizing unit 50 analog to digital input (for sensors) or the Analog High Voltage amplifier 70 (for actuators) and then to the digital to analog output of the digitizing unit 50. In some alternative configurations, two sets of wires 2 may provide backup functionality from an open circuit failure. In some embodiments, each side of the PZT transducer may have connections to top and bottom inter-digitizing grids facilitating this function.

In the present embodiment, a wireless communication link 20 may be the electronic link to record the data collected by a computer. Link 20 may typically use current technology such as, but not limited to, Wi-Fi, Cellular, etc. and may depend on the application. This may enable remote access. A computer 30 may be used for data, control, and analysis. In some embodiments, computer 30 may be an embedded design with programing retained on a chip. In other embodiments, computer 30 may be, without limitation, a standard or laptop computer which may be connected over Ethernet or wireless. In some embodiments, the control, data and analysis software may be coded in MATLAB® for much of the applications, but other software may be used such as, but not limited to, LabVIEW®. In the present embodiment, the digitizing interface 50 may be an electronic module with analog to digital inputs and digital to analog output along with discrete capability such as, but not limited to, 0-5-volt. The electronics supply voltage is shown by the battery/power supply 40.

Figure 2:
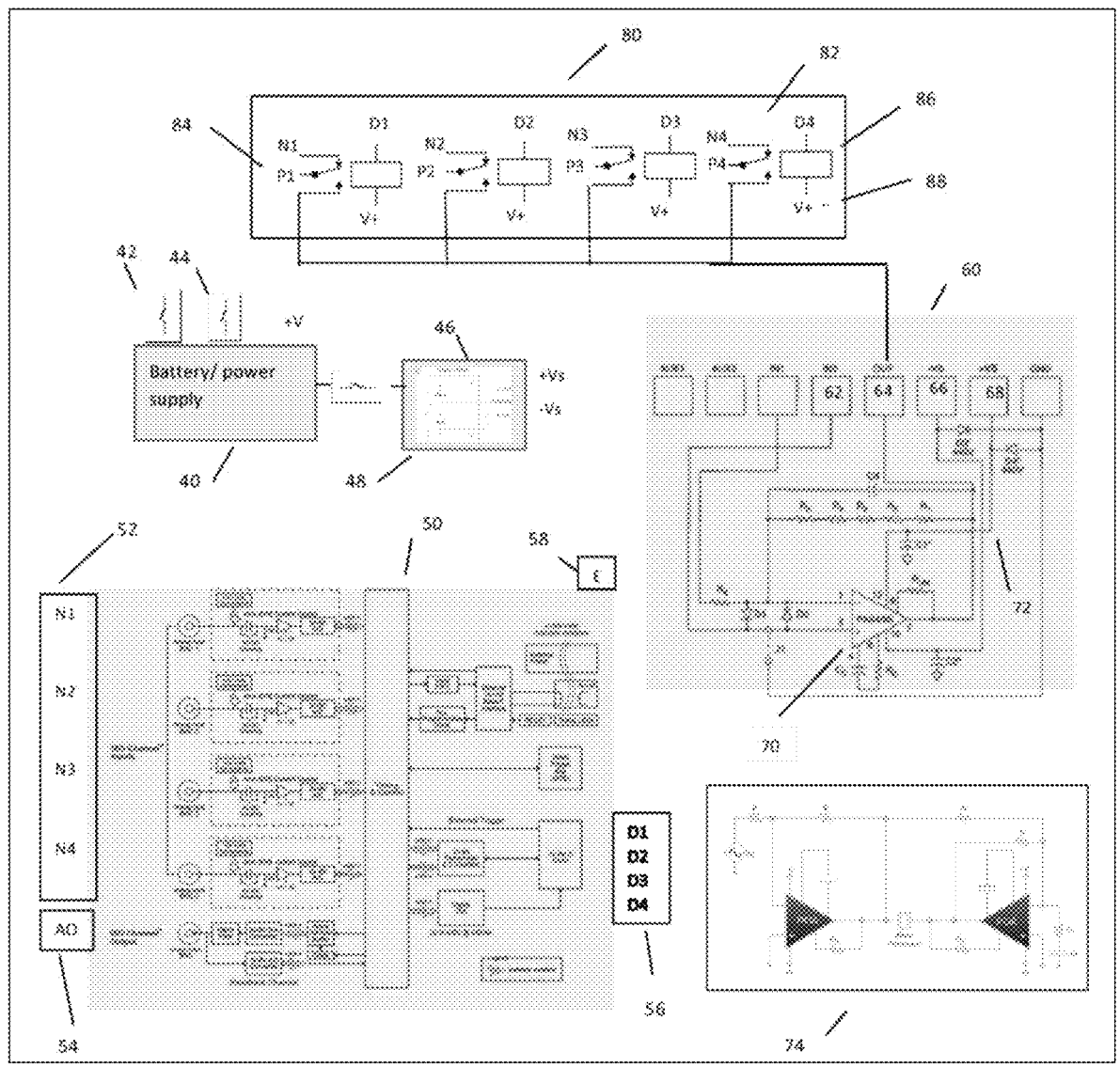
FIG. 2 is an illustration of details of relay unit, high voltage amplifier, and digitizing unit, in accordance with an embodiment of the present invention.

FIG. 2 is an illustration of details of relay unit, high voltage amplifier, and digitizing unit, in accordance with an embodiment of the present invention. A Data Translation 50 model DT8837 is shown. In other embodiments, functionally equal designs may be used. Some characteristics of data translation 50 may be:

4 or more Simultaneous, 24-bit Delta-Sigma A/D channels;

Minimum 52.7 kS/s/ch sample rate;

One 24-bit D/A converter;

4 or more Isolated Digital Outputs, ±30V @ 400 mA;

Multiple module synchronization via the Trigger Bus for channel expansion. These modules may be synchronized via a Wired Trigger Bus and may be externally triggered in various ways;

IVI-COM driver which works in any 32-bit development environment that supports COM programming, including MATLAB® and Lab VIEW®; and TCP/IP Ethernet operation allows measurements to be monitored locally or at other remote sites. Other embodiments may have differing characteristics depending on application.

In the present embodiment, the digitizing interface 50 may convert the analog sensor signals with high precision and over a broad frequency range of, but not limited to, 1-100,000 Hz with typically used data rates of 12,800 samples per second (sps), 25,600 and 51,200 sps. N1-N4 52 are inputs to the A to D channels from the PZT transducers, four are shown but more channels may be used up to the limit of the hardware. In the use of the DT8837 50 up to 64 channels may be used using a module synchronization feature. The digitizing interface 50 has an analog output AO 54 which may use a computer program random function to output a random white noise of, but not limited to, (0-10 volts AC) to a high voltage amplifier 60 IN 62 which connects through electrical interface circuit 72 to an AMPEX PA95 OP AMP 70 (or equivalent component). In other embodiments, other amplifiers may be used. The digitizing unit 50 DI-D4 56 discrete voltages activate the relay switching device 80 relay coils 86. The voltage to power the relay may be from the Battery/power supply 40. In the present embodiment, the Battery/power supply 40 may provide 12-24 volts DC for the digitizing unit 50 through switch 42, computer 30 through switch 44 and to DC to DC high voltage convertor 48 through switch 46. In other embodiments, the requirements of power supply 40 may vary as well as the switching. In some embodiments, the switches 42, 44 and 46 may be cycled on/off locally or with additional electronics over the internet (not shown). In the present embodiment, digitizing unit 50 may connect to the computer 30 via Ethernet E 58. In other alternative embodiments, other protocols may be utilized such as, but not limited to, USB cable and protocol, etc.

In the present embodiment, amplifier 70 may provide a high voltage low current signal over a broad frequency range of, but not limited to, (1-50,000 Hz) to drive the PZT actuator(s) 4 or 6. The supply voltage +Vs 66 and −Vs 68 comes from a DC to DC convertor 48. In some embodiments, the frequency range may depend on the application such as, without limitation, response and transmission frequencies for that material/geometry/weight and stiffness which is influence by environmental effects such as, without limitation, temperature and internal material strain. In a non-limiting example, recent tests at NASA Glen Research Center show that with the vibration of a rocket engine firing under low pressure and low temperature environments to simulate outer space, the mass shifting frequencies due to liquid oxygen tank use may be easily shown by embodiments of the present invention. In a non-limiting example, typically tested ranges may be 2-10,000, 2-25,000 Hz. In the present embodiment, the digitizing relay switch box 80 is a digital relay switch box which may allow software through the data acquisition module digitized output function to control which PZT transducer P1-P4 84 is used for sensors (relay 82 Normally closed) or selected to as an actuator (relay 82 energized). The actuator and sensor transducers are interchangeable. By applying the actuator random white noise at various points, a very large structure may be interrogated. In a non-limiting example, very large all composite tanks have been tested of about 5.2 meters in diameter and with a sufficient signal to show a modal response from the tank. This relay switch box 80 is optional and may not be required for some applications. The electrical power for the electronics is provided by the Battery/power supply 40 (12-24 volts DC) which may utilize rechargeable batteries.

Figure 3:
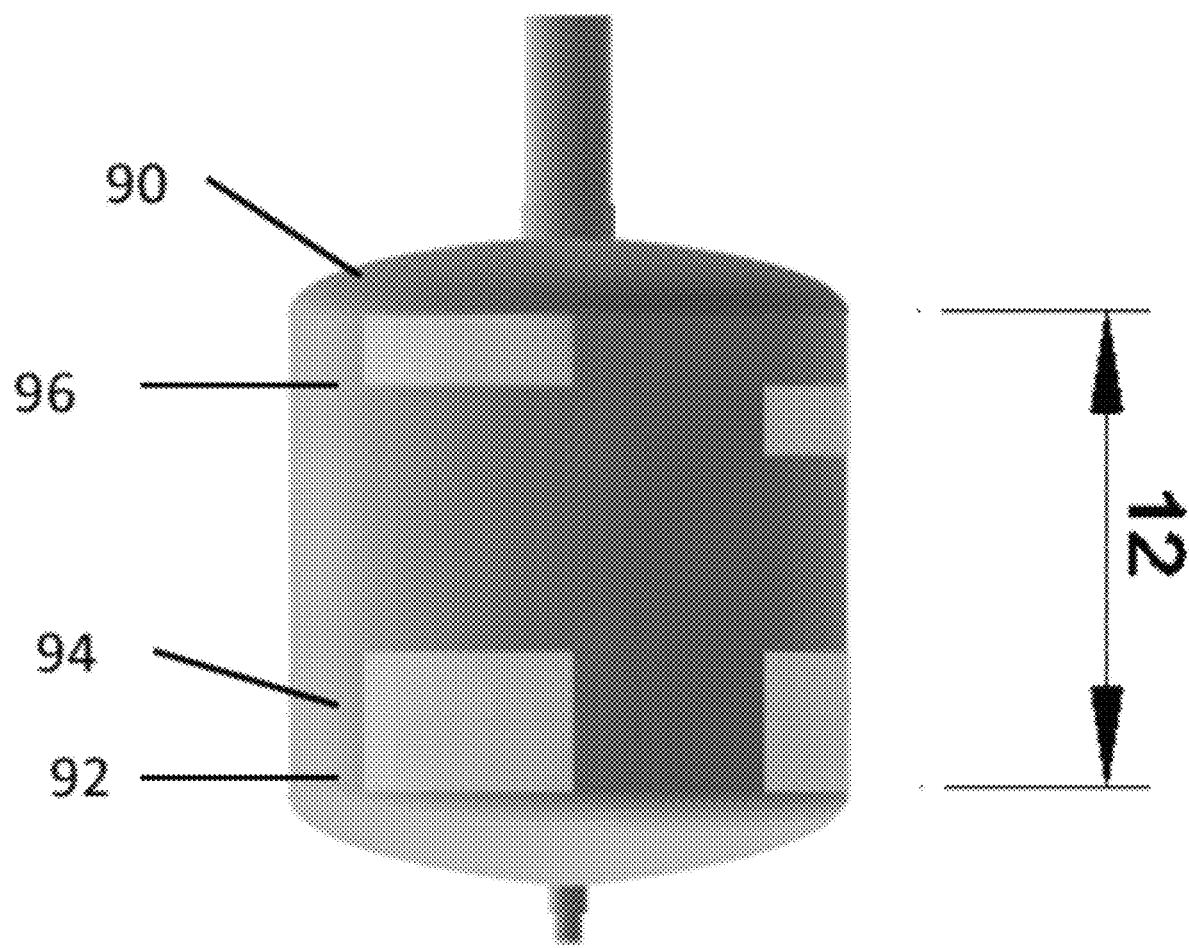
FIG. 3 is an illustration of a typical experimental tank for mass measurement under zero-g, the Inner wall shows PZT actuator and sensor 1 locations. For cryogenic use these is a vacuum/insulated annulus with an outer wall not shown which minimizes fluid loss, in accordance with an embodiment of the present invention.

FIG. 3 is an illustration of a typical experimental tank for mass measurement under zero-g, the Inner wall shows PZT actuator and sensor 1 locations. For cryogenic use these is a vacuum/insulated annulus with an outer wall not shown which minimizes fluid loss, in accordance with an embodiment of the present invention. In the present embodiment, a typical experimental tank 90 for zero-g mass measurement is shown. In some embodiments, if used for cryogenic fluids, there may be an inner tank with sensors/actuators attached located in the annulus with vacuum/insulation the electrical connections to the transducers outside the outer wall. In the present embodiment, the referenced dimension is 12 inches. A lower PZT transducer 92 is used as an actuator, with a response PZT sensor 94 along a vertical side. A second response PZT sensor 96 is a vertical near the upper cylinder section. Additional sensors a located about 90 degrees off this axis may provide backup and additional FRF pairs if required to collect the strongest responses. As a non-limiting example, the lower modes of this liquid filled cylinder has experimentally shown to produce some of the best data in which the fluid level (mass) is related to the frequencies by shifting lower as the mass is increased. It is believed that this is true under Earth's gravity or in micro gravity (near zero g) of the parabolic aircraft environments.

Figure 4:
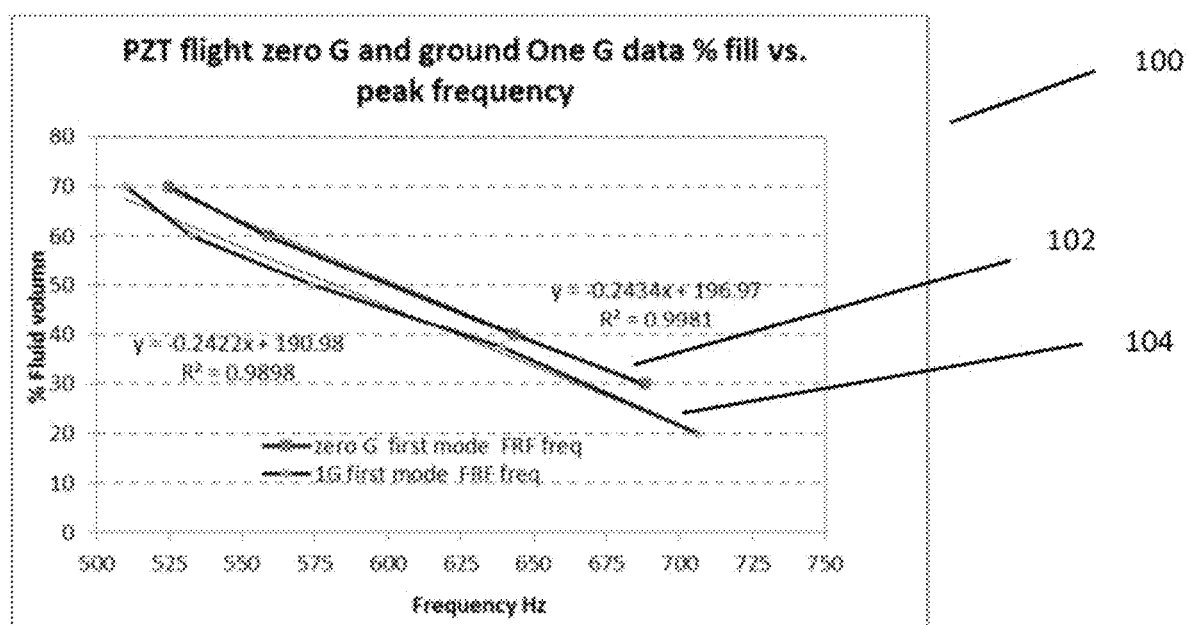
FIG. 4 shows the experimental data from Parabolic Plane Zero G experiments showing the PZT vibration system used for non-invasive zero (micro) gravity fluid mass measurements using water as a fluid, in accordance with an embodiment of the present invention.

FIG. 4 shows the experimental data from Parabolic Plane Zero G experiments showing the PZT vibration system used for non-invasive zero (micro) gravity fluid mass measurements using water as a fluid, in accordance with an embodiment of the present invention. A Graph 100 shows analyzed data showing the Parabolic Plane Zero G (micro g) 20 second periods experiment % water level vs. frequency, data from the FRF's using sensor locations 94 and 96 with actuator 92 providing random input vibration. The FRF's used 2-5 averages to allow for fluid movement in tank sloshing due to residual effects of the g forces on the system and the short duration of the zero-g phase. The Graph 100 vertical axis is percent of fluid volume in the tank with the horizontal axis showing a FRF mode frequency in Hertz. The top set of data 102 has a nearly linear relationship of volume to frequency for the 20 second zero g phases. Four tank level data points are shown from repeated parabolic flight profiles where data was collected. The tank level was adjusted during the gravity phases of the flight profile. The best fit line is shown above the line showing a goodness of fit $R2=0.9981$ indicating the invention zero-g fluid mass provides high accuracy over the tested levels of 20-70%. The graph second line 104 shows the experiment data taken over similar tank fill levels while on the ground (1 g) prior to flight. The goodness of fit $R2=0.9898$ which is actually lower than the zero g data, but still very good. The difference may be accounted for by more electrical noise in the data on the ground data.

Figure 5:
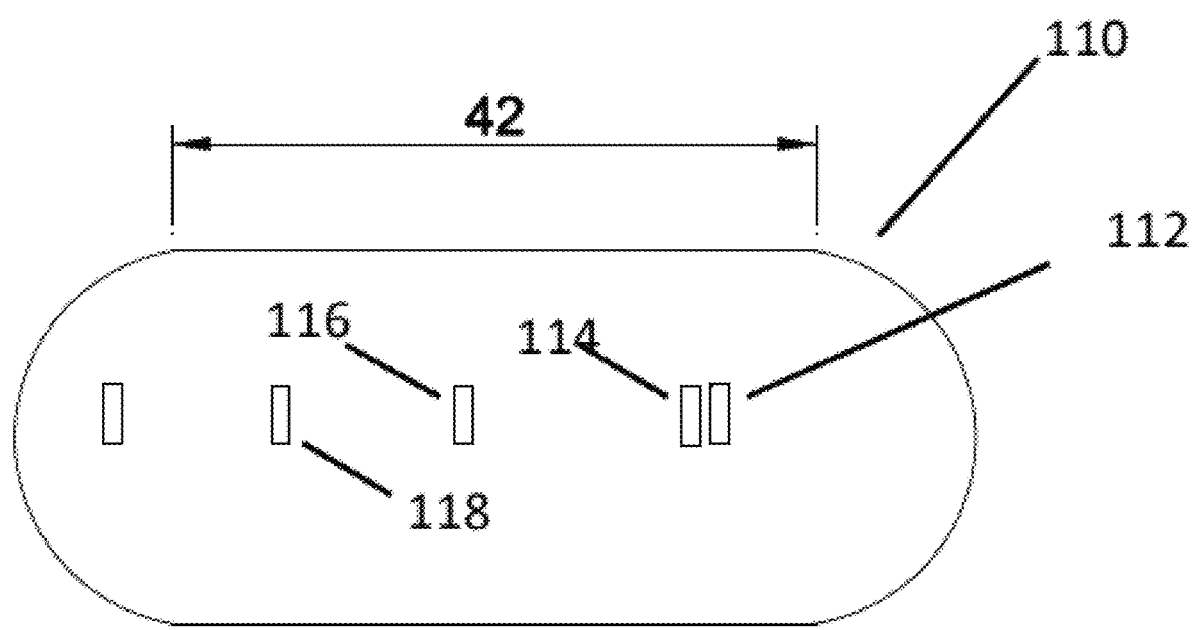
FIG. 5 is an illustration of a 100 gallon COPV tank showing PZT actuator and sensors, in accordance with an embodiment of the present invention.

FIG. 5 is an illustration of a 100 gallon COPV tank showing PZT actuator and sensors, in accordance with an embodiment of the present invention. A 100-gallon Composite Overwrap Pressure vessel (COPV) 110 used for experimental data which was filled with cryogenic fluid (liquid Nitrogen) with the present invention recording approximately 20 second intervals of active random input vibration data after each increasing pressure steps until failure. A length of a cylindrical section is 42 inches as shown in the figure. Larger and smaller tanks 500-2 gallons including all composite tanks have similarly been tested to failure with the invention health monitoring. A lower transducer 112 was used as an actuator with a nearest transducer 114 as the input response like in prior experiments. Additional transducers were located at the mid-section 116, and upper section 118 and top dome. The total number of transducers is only limited by channels but is keep minimal for practically and depending on the application including size of tank, materials and type of fluid. Experiments indicate the spacing of the response sensors may extend to several meters or more still with sufficient actuator vibration levels to stimulate many structural modes. The tank was held vertically and filled with liquid nitrogen with gas pressure being applied in pressure steps with approximately 20 second intervals of active random input vibration data recorded after each increasing step. The pressure was maintained at the same level between steps (near 0 psig) so as not to affect the stiffness with another variation. Higher tank pressures proportionally increases stiffness (increase mode frequencies) and the experiment was to compare only frequency variations due to damage in the tank.

Figure 6:
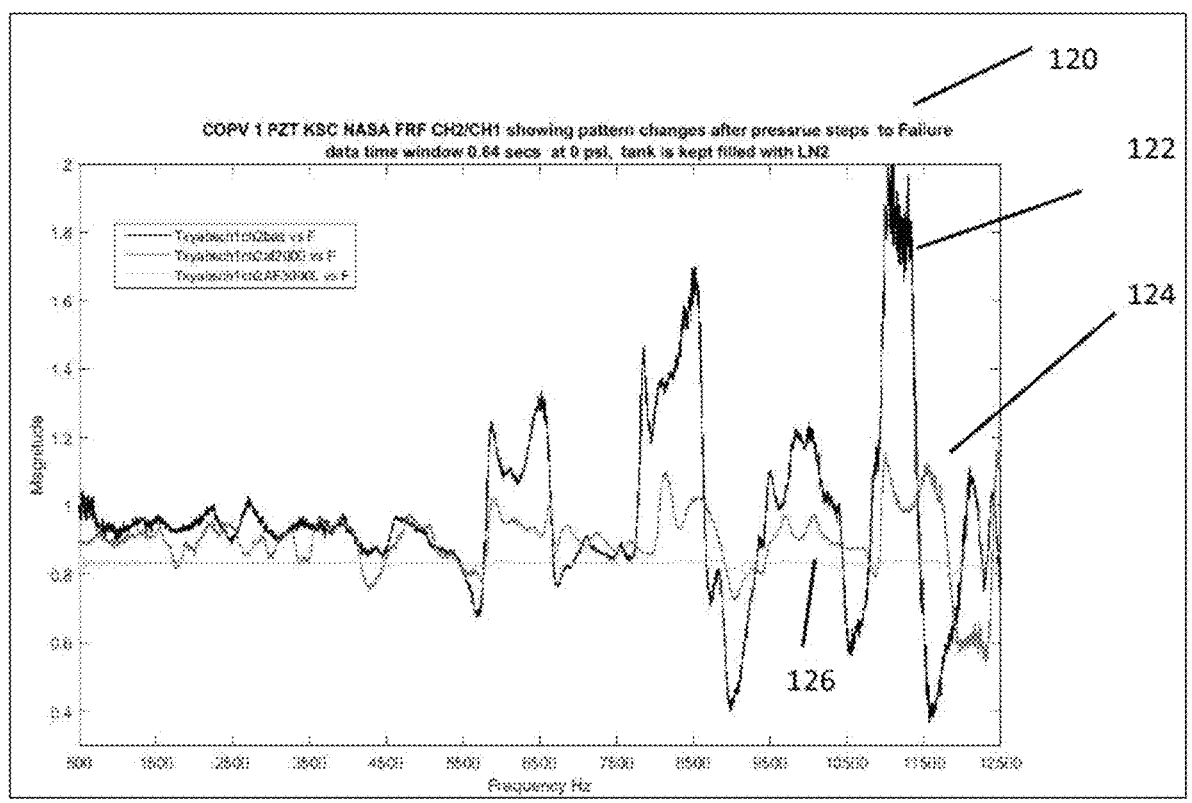
FIG. 6 shows the frequency signature comparing the baseline (undamaged) to several damaged states shown after pressure steps 2000 psig and 3000 psig burst occurred at 3150 psig, in accordance with an embodiment of the present invention.

FIG. 6 shows the frequency signature comparing the baseline (undamaged) to several damaged states shown after pressure steps 2000 psig and 3000 psig burst occurred at 3150 psig, in accordance with an embodiment of the present invention. A Graph 120 shows FRF signature changes as COPV/composite tanks are pressurized which causes accumulating damage. Areas under the FRF peaks and/or standard deviation is useful as software indicators as to when damage requires stopping use. The Graph 120 vertical is axis is relative magnitude with the horizontal axis units of frequency in Hertz (500-12500 Hz shown). The largest peaks and highest Standard deviation of the Graph signatures FRF (FFT sensor 118/FFT sensor 116), vibration signature 122 are from the baseline recording with actuator active for ~20 seconds, the FFT time window is 0.6 seconds, data digitizing sampling rate of 25,600 per second the temperature is stable with near zero pressure just prior to pressure steps. The Graph FRF signature are also shown after 2000 psig step 124 by the mid-range modal peak magnitudes across the displayed frequencies (500-12500 Hz). Conditions are similar to the baseline (temperature is stable with near zero pressure). The final Graph FRF plot 126 is after the 3000 psig step the signature has the lowest magnitude, Conditions are again similar to the baseline (temperature is stable with near zero pressure). The three plots are representative of the data and points to a degraded conditions in the tank structure that primary affects damping and magnitude accumulated damage possibly due to micro cracking and deboning in the composite matrix (but not fiber breakage-yet) The tank failed with center fiber failure and tank brake-up as pressure was increased to 3150 psig. A series of others experiments confirm the invention usefulness to detect structural changes before failure, with only periodic activation (relatively small file sizes and simple analysis is possible) The invention does not produce a wave based reflected map of insignificant structural changes as other NDE and health methods can—which greatly complicates analysis, producing large volumes of unimportant data. The invention simple analysis uses a single number such as, but not limited to, area under the modal peaks, standard deviation, frequency mode shifts or cross correlation of the FRF frequencies which can be used for a go/no-go software flag. This Invention enables in-Sutu damage detection over the entire usage life of the structure/tank.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Figure 7:
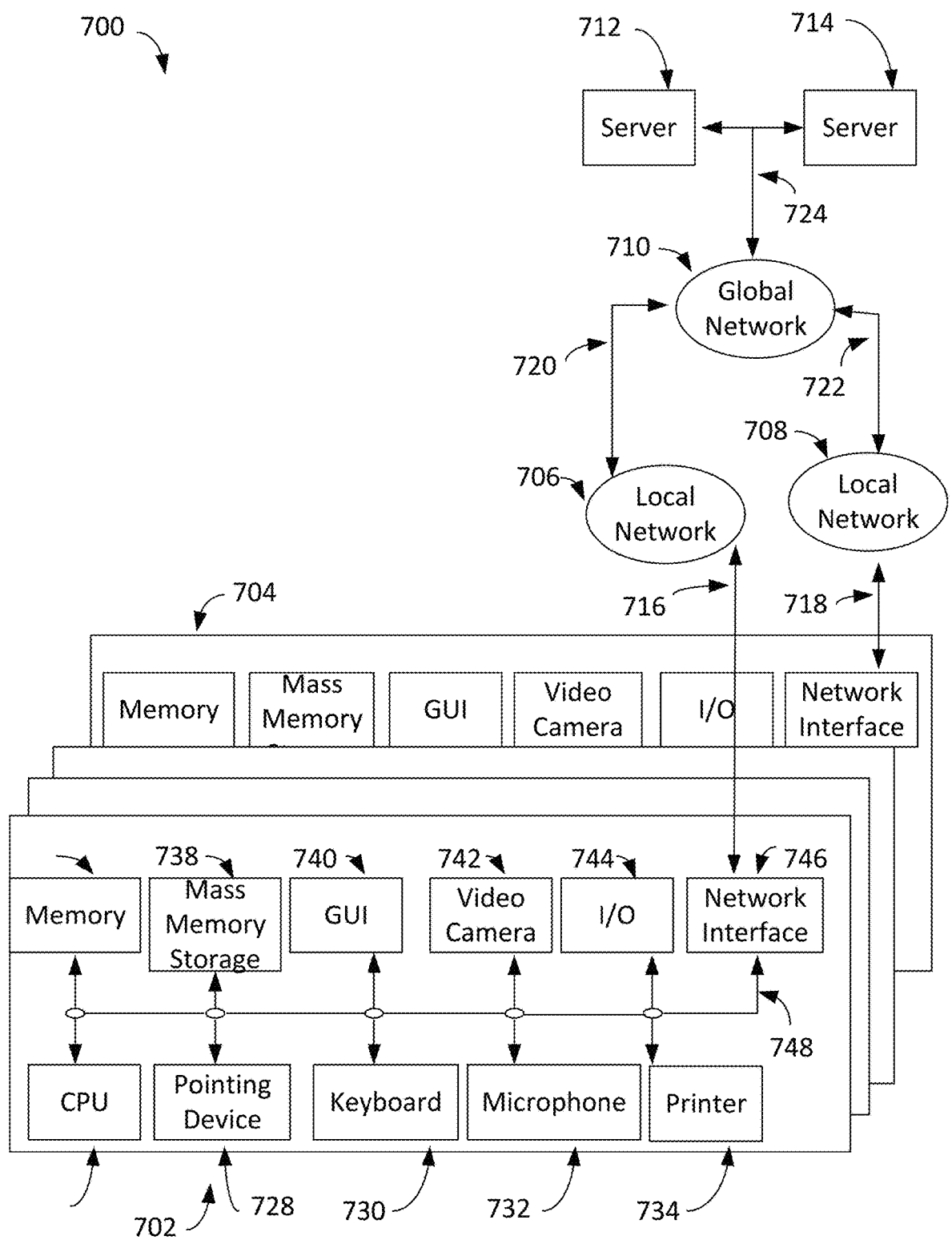
FIG. 7 is a block diagram depicting an exemplary client/server system which may be used by an exemplary web-enabled/networked embodiment of the present invention.

FIG. 7 is a block diagram depicting an exemplary client/server system which may be used by an exemplary web-enabled/networked embodiment of the present invention.

A communication system 700 includes a multiplicity of clients with a sampling of clients denoted as a client 702 and a client 704, a multiplicity of local networks with a sampling of networks denoted as a local network 706 and a local network 708, a global network 710 and a multiplicity of servers with a sampling of servers denoted as a server 712 and a server 714.

Client 702 may communicate bi-directionally with local network 706 via a communication channel 716. Client 704 may communicate bi-directionally with local network 708 via a communication channel 718. Local network 706 may communicate bi-directionally with global network 710 via a communication channel 720. Local network 708 may communicate bi-directionally with global network 710 via a communication channel 722. Global network 710 may communicate bi-directionally with server 712 and server 714 via a communication channel 724. Server 712 and server 714 may communicate bi-directionally with each other via communication channel 724. Furthermore, clients 702, 704, local networks 706, 708, global network 710 and servers 712, 714 may each communicate bi-directionally with each other.

In one embodiment, global network 710 may operate as the Internet. It will be understood by those skilled in the art that communication system 700 may take many different forms. Non-limiting examples of forms for communication system 700 include local area networks (LANs), wide area networks (WANs), wired telephone networks, wireless networks, or any other network supporting data communication between respective entities.

Clients 702 and 704 may take many different forms. Non-limiting examples of clients 702 and 704 include personal computers, personal digital assistants (PDAs), cellular phones and smartphones.

Client 702 includes a CPU 726, a pointing device 728, a keyboard 730, a microphone 732, a printer 734, a memory 736, a mass memory storage 738, a GUI 740, a video camera 742, an input/output interface 744 and a network interface 746.

CPU 726, pointing device 728, keyboard 730, microphone 732, printer 734, memory 736, mass memory storage 738, GUI 740, video camera 742, input/output interface 744 and network interface 746 may communicate in a unidirectional manner or a bi-directional manner with each other via a communication channel 748. Communication channel 748 may be configured as a single communication channel or a multiplicity of communication channels.

CPU 726 may be comprised of a single processor or multiple processors. CPU 726 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 736 is used typically to transfer data and instructions to CPU 726 in a bi-directional manner. Memory 736, as discussed previously, may include any suitable computer-readable media, intended for data storage, such as those described above excluding any wired or wireless transmissions unless specifically noted. Mass memory storage 738 may also be coupled bi-directionally to CPU 726 and provides additional data storage capacity and may include any of the computer-readable media described above. Mass memory storage 738 may be used to store programs, data and the like and is typically a secondary storage medium such as a hard disk. It will be appreciated that the information retained within mass memory storage 738, may, in appropriate cases, be incorporated in standard fashion as part of memory 736 as virtual memory.

CPU 726 may be coupled to GUI 740. GUI 740 enables a user to view the operation of computer operating system and software. CPU 726 may be coupled to pointing device 728. Non-limiting examples of pointing device 728 include computer mouse, trackball and touchpad. Pointing device 728 enables a user with the capability to maneuver a computer cursor about the viewing area of GUI 740 and select areas or features in the viewing area of GUI 740. CPU 726 may be coupled to keyboard 730. Keyboard 730 enables a user with the capability to input alphanumeric textual information to CPU 726. CPU 726 may be coupled to microphone 732. Microphone 732 enables audio produced by a user to be recorded, processed and communicated by CPU 726. CPU 726 may be connected to printer 734. Printer 734 enables a user with the capability to print information to a sheet of paper. CPU 726 may be connected to video camera 742. Video camera 742 enables video produced or captured by user to be recorded, processed and communicated by CPU 726.

CPU 726 may also be coupled to input/output interface 744 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 726 optionally may be coupled to network interface 746 which enables communication with an external device such as a database or a computer or telecommunications or internet network using an external connection shown generally as communication channel 716, which may be implemented as a hardwired or wireless communications link using suitable conventional technologies. With such a connection, CPU 726 might receive information from the network, or might output information to a network in the course of performing the method steps described in the teachings of the present invention.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6). In some alternative embodiments, the use of fiber optical based transducers such as, but not limited to, Fiber Bragg Grating (FBG) based (as sensors only) may be also viable. This technology may allow many small sensors with no electrical noise effects or sensitivity. This may be a hybrid system using a PZT actuator and fiber optic response sensors.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112 (6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing the use of vibration signatures to monitor an instrumented structure or tank according to the present invention will be apparent to those skilled in the art. Various aspects of the invention have been described above by way of illustration, and the specific embodiments disclosed are not intended to limit the invention to the particular forms disclosed. The particular implementation of the use of vibration signatures to monitor an instrumented structure or tank may vary depending upon the particular context or application. By way of example, and not limitation, the use of vibration signatures to monitor an instrumented structure or tank described in the foregoing were principally directed to structural health monitoring and/or non-invasive tank fluid level measurement including cryogenic and zero g environments implementations; however, similar techniques may instead be applied to structural health monitoring and/or non-invasive tank non-fluid level measurement including powder, grains, solids, etc., which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A system comprising:
a first transducer configured as an actuator, said first transducer adapted to be coupled to a surface of a structure;
a second transducer configured as a sensor, said second transducer adapted to be coupled to the surface at a first distance from said first transducer;
a third transducer configured as a sensor, said third transducer adapted to be coupled to the surface at a second distance from said first transducer, wherein said second distance is greater than said first distance;
a digitizing unit being at least configured for communicating random white noise signals to said first transducer, said digitizing unit being at least further configured for receiving signals originating from said second transducer and said third transducer as said first transducer receives the random white noise signals; and
a computing unit being at least configured for
Communicating the random white noise signals to said digitizing unit,
receiving the signals from said digitizing unit that originate from said second transducer and said third transducer,
generating a fast Fourier transform (FFT) for each of the signals received from said digitizing unit that originate from said second transducer and said third transducer, and
dividing the FFT generated from the signals originating from said third transducer by the FFT generated from the signals originating from said second transducer to thereby generate a Frequency Response Function, wherein changes to the Frequency Response Function indicate a change to physical properties of the structure.

2. The system as recited in claim 1, further comprising a relay unit at least configured for directing signals between said digitizing unit, said first transducer, said second transducer, and said third transducer.

3. The system as recited in claim 1, further comprising an amplifying unit being at least configured for amplifying the random white noise signals communicated to said digitizing unit.

4. The system as recited in claim 1, further comprising a wireless communication link being at least configured for remote access to said computing unit.

5. The system as recited in claim 1, in which the physical properties of the structure at least comprises underlying stiffness and modal mass of the structure.

6. The system as recited in claim 1, in which said first transducer, said second transducer, and said third transducer comprise identical piezoelectric transducers.

7. The system as recited in claim 6, in which said piezoelectric transducers further comprise Interdigitated Electrodes.

8. The system as recited in claim 1, further comprising a plurality of additional piezoelectric transducers positioned on the surface.

9. The system as recited in claim 1, in which the structure further comprises a tank.

10. The system as recited in claim 9, in which the tank further comprises composite materials and the tank is at least configured for cryogenic containment.

11. The system as recited in claim 10, in which the Frequency Response Function indicates an amount and mass of fluid in contact with an inner wall of the tank when the tank is adapted to be in a near zero-G environment.

12. A system comprising:
at least three piezoelectric transducers adapted to be in contact with a surface of a structure, said at least three piezoelectric transducers each further comprising Interdigitated Electrodes, said at least three piezoelectric transducers being non-intrusive to the surface and identical in construction, said at least three piezoelectric transducers each being configurable as an actuator and configurable as a sensor;
a digitizing unit at least configured for communicating a plurality of frequency signals to a first of said at least three piezoelectric transducers, the plurality of frequency signals comprising random white noise extending from approximately 1 Hertz up to an ultrasonic range, said digitizing unit being at least further configured for receiving signals originating from a second and a third of said at least three piezoelectric transducers as said first transducer receives the plurality of frequency signals, wherein said first and said second of said at least three piezoelectric transducers are separated by a first distance, wherein said first and said third of said at least three piezoelectric transducers are separated by a second distance, and wherein said second distance is greater than said first distance;
an amplifying unit being at least configured for amplifying the plurality of frequency signals from said digitizing unit;
a relay unit being at least configured for directing signals between said digitizing unit and said at least three piezoelectric transducers;
a computing unit being at least configured for
communicating the plurality of frequency signals to said digitizing unit,
receiving the signals from said digitizing unit originating from said second and said third of said at least three piezoelectric transducers as said first of said at least three piezoelectric transducers receives the plurality of frequency signals,
generating a fast Fourier transform (FFT) for each of the signals received from said digitizing unit that originate from said second and said third of said at least three piezoelectric transducers, and
dividing the FFT generated from the signals originating from said third of said at least three piezoelectric transducers by the FFT generated from the signals originating from said second of said at least three piezoelectric transducers to thereby generate a Frequency Response Function, wherein changes to the Frequency Response Function indicate a change to physical properties of the structure, the physical properties of the structure comprising an underlying stiffness and modal mass of the structure; and
a wireless communication link being at least configured for remote access to said computing unit.

13. The system as recited in claim 12 further comprising a plurality of additional piezoelectric transducers adapted to be positioned on the surface and in which the structure further comprises a tank comprising composite materials and at least configured for cryogenic containment, the Frequency Response Function indicating an amount and mass of fluid in contact with an inner wall of the tank when the tank is adapted to be in a near zero-G environment.

* * * * *